US008926489B2

(12) United States Patent
Brunson et al.

(10) Patent No.: US 8,926,489 B2
(45) Date of Patent: Jan. 6, 2015

(54) HYPODERMIC NEEDLE CONTAINMENT SYSTEM

(76) Inventors: Robert W. Brunson, Ogden, UT (US); Jeremy Sorensen, West Jordan, UT (US)

(*) Notice: Subject to any disclaimer, the term of this patent is extended or adjusted under 35 U.S.C. 154(b) by 58 days.

(21) Appl. No.: 13/551,547

(22) Filed: Jul. 17, 2012

(65) Prior Publication Data

US 2014/0024877 A1    Jan. 23, 2014

(51) Int. Cl.
*B65D 81/00*    (2006.01)
*A61B 19/02*    (2006.01)

(52) U.S. Cl.
CPC .................................... *A61B 19/0288* (2013.01)
USPC ........................................ 588/249.5; 206/364

(58) Field of Classification Search
USPC ................ 588/252, 249.5; 206/363–366
See application file for complete search history.

(56) References Cited

U.S. PATENT DOCUMENTS

| | | | | |
|---|---|---|---|---|
| 3,585,275 A | * | 6/1971 | Gillemot et al. | 174/76 |
| 4,728,321 A | * | 3/1988 | Chen | 604/110 |
| 4,758,229 A | * | 7/1988 | Doerschner | 604/187 |
| 4,845,923 A | * | 7/1989 | Donovan | 53/431 |
| 4,875,896 A | * | 10/1989 | Kurtz | 604/187 |
| 5,084,027 A | * | 1/1992 | Bernard | 604/192 |
| 5,133,454 A | * | 7/1992 | Hammer | 206/364 |
| 5,352,200 A | * | 10/1994 | Hammett et al. | 604/110 |
| 5,368,580 A | * | 11/1994 | Suzuki | 604/263 |
| 5,383,862 A | * | 1/1995 | Berndt et al. | 604/187 |
| 5,407,070 A | * | 4/1995 | Bascos et al. | 206/365 |
| 5,538,132 A | * | 7/1996 | Propp et al. | 206/365 |
| 5,554,131 A | * | 9/1996 | Lacivita | 604/198 |
| 6,315,113 B1 | * | 11/2001 | Britton et al. | 206/210 |
| 6,485,474 B1 | * | 11/2002 | Heinz et al. | 604/263 |
| 8,172,104 B2 | * | 5/2012 | Weber | 220/62 |

FOREIGN PATENT DOCUMENTS

GB    2283917 A    *    5/1995    ............ A61B 19/02

* cited by examiner

*Primary Examiner* — John Kreck
(74) *Attorney, Agent, or Firm* — Michael F. Krieger; Kirton McConkie

(57) ABSTRACT

Containment systems and methods safely and permanently encapsulate a sharp portion of a sharp medical instrument (e.g. a hypodermic needle). The containment system includes a cap or other container formed of a durable and flexible material and having a rim defining an open end configured to receive the sharp portion therein and an adhesive disposed on an interior surface of the container. The method of use includes inserting the sharp medical instrument into the container, and compressing the sides of the container to permanently encapsulate the sharp portion of the medical instrument within the adhesive. The adhesive may be an adhesive tape and may be protected before use by a covering, which may be removed at the time of use by pulling a pull tab extending from an opening in the container.

14 Claims, 3 Drawing Sheets

HYPODERMIC NEEDLE CONTAINMENT SYSTEM

BACKGROUND OF THE INVENTION

1. Field of the Invention

The present invention relates to containment systems for hypodermic needles and other sharp medical instruments, and more particularly to containment systems permanently encapsulating and containing hypodermic needles to prevent reuse and accidental needle sticks.

2. Background and Related Art

The handling and disposal of used medical instruments, particularly sharp medical instruments such as hypodermic needles, suture needles, lancets, trocars, scalpel blades and the like is a major problem facing healthcare professionals. Blood-born pathogens can be easily transmitted by inadvertent contact with the used medical instrument such as by accidental needle sticks.

In order to avoid such accidental needle sticks, especially immediately after using the needle, the healthcare professional will attempt to cover the needle with a protective cap or sheath so that the instrument can be safely transported for disposal. The provision for caps and sheaths affords some degree of protection, however many accidental needle sticks occur while trying to place the cap or sheath back on the needle in preparation for transport for disposal.

In the absence of re-capping or re-sheathing, quite often the used medical instrument is transported uncovered to a sharps container which ideally is located proximate to the site. The sharps container holds several used medical instruments in a hard puncture-resistant package which is subsequently collected for final disposal. However, this still requires the healthcare professional to handle and transport the unprotected needle after use. Also, the collected used instruments remain on site in the sharps container until collected for final disposal.

The art has seen many devices for capping, closing and sheathing used sharp medical instruments for disposal. Many of these devices simply enclose the entire medical instrument, or at least the sharp portion thereof in a protective enclosure. Other of these devices attempt to encapsulate or surround the used medical instrument with a composition which hardens around the sharp portion of the instrument, providing permanent containment and protection.

One such encapsulation system uses a two-part hardenable compound provided in a container (e.g. a needle cover) which accepts a sharp medical instrument such as a hypodermic needle. The container supports a hardenable resin such as a cyanoacrylate ester and a filler of particulate matter in spaced separation. The filler includes an accelerator which is used to speed up the hardening of the resin. The resin and the filler accelerator are separated by a rupturable partition such as thin glass. The used medical instrument, such as a needle, is inserted into the container, rupturing the glass membrane between the two components, thereby causing the components to come together and harden around the needle.

Such encapsulation systems have several disadvantages. First, it can be difficult and hence expensive to properly manufacture such systems, as the small scale of such systems necessitates care and precision in manufacturing. If any manufacturing deficiencies allow the two-part hardenable compound to mix before the intended time, the attempt to insert the needle into the encapsulation system may fail, and an additional system will be needed. Additionally, such systems, of necessity require two separate devices for protecting the hypodermic needle before and after use: a standard cap or cover for protecting the needle before use, and an encapsulation cap or cover for after use of the needle. The use of multiple caps or covers results in extra waste, extra costs, extra time spent seeking to ensure that the correct cap or cover is used, etc. Finally, such systems may be prone to inadequate mixing of the two-part hardenable compound, such that permanent encapsulation of the needle is not achieved.

BRIEF SUMMARY OF THE INVENTION

Implementation of the invention provides a containment system for encapsulating a sharp medical instrument. The containment system includes a container formed of a durable and flexible material having a rim defining an open end configured to receive a sharp portion of the medical instrument and an interior surface, wherein at least a portion of the interior surface is covered with a strong adhesive such that opposing sides of the container can be deformed under external pressure to cause the opposing sides to come together surrounding the sharp portion such that the sharp portion is substantially permanently retained inside the container by the adhesive.

The sharp medical instrument may be a hypodermic needle, and the container a cap of the needle. The adhesive may be protected by a removable covering. The removable covering may be attached to a pull tab that extends through an opening in an end of the container distal the open end defined by the rim.

The container may have a cross-section having a major axis and a minor axis, and wherein the container is deformable in the direction of the minor axis to permit opposite sides of the container to compress along the minor axis until they contact one another. The container may have a generally-oval cross section.

The adhesive may be an adhesive tape disposed on the interior surface. The adhesive tape may be protected by a removable covering attached to a pull tab that extends through an opening in an end of the container distal the open end defined by the rim.

Further implementation of the invention provides a method for safely and permanently encapsulating a sharp medical instrument. The method includes inserting the sharp medical instrument into a container having a rim defining an open end configured to receive a sharp portion of the medical instrument and an interior surface, wherein at least a portion of the interior surface is covered with a strong adhesive. The method also includes causing opposing sides of the container to be deformed under external pressure and to be brought together surrounding the sharp portion such that the sharp portion is substantially permanently retained inside the container by the adhesive.

The sharp medical instrument may be a hypodermic needle, and the container a cap for the needle.

The method may also include removing a removable covering protecting the adhesive before deforming the opposing sides of the container. Removing the removable covering may include pulling a pull tab that extends through an opening in an end of the container distal the open end defined by the rim.

The container may have a cross-section having a major axis and a minor axis, and wherein the container is deformable in the direction of the minor axis to permit opposite sides of the container to compress along the minor axis until they contact one another.

Implementation of the invention provides a containment system for encapsulating a hypodermic needle. The system includes a cap formed of a durable and flexible material having a rim defining an open end configured to receive the needle and an interior surface, wherein at least a portion of the interior surface is covered with a strong adhesive such that opposing sides of the cap can be deformed under external pressure to cause the opposing sides to come together surrounding the needle such that the needle is substantially permanently retained inside the cap by the adhesive.

The adhesive may be protected by a removable covering. The removable covering may be attached to a pull tab that extends through an opening in an end of the cap distal the open end defined by the rim.

The cap may have a cross-section having a major axis and a minor axis, wherein the cap is deformable in the direction of the minor axis to permit opposite sides of the cap to compress along the minor axis until they contact one another. The cap may have a generally-oval cross section.

The adhesive may be an adhesive tape disposed on the interior surface. The adhesive tape may be protected by a removable covering attached to a pull tab that extends through an opening in an end of the cap distal the open end defined by the rim.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
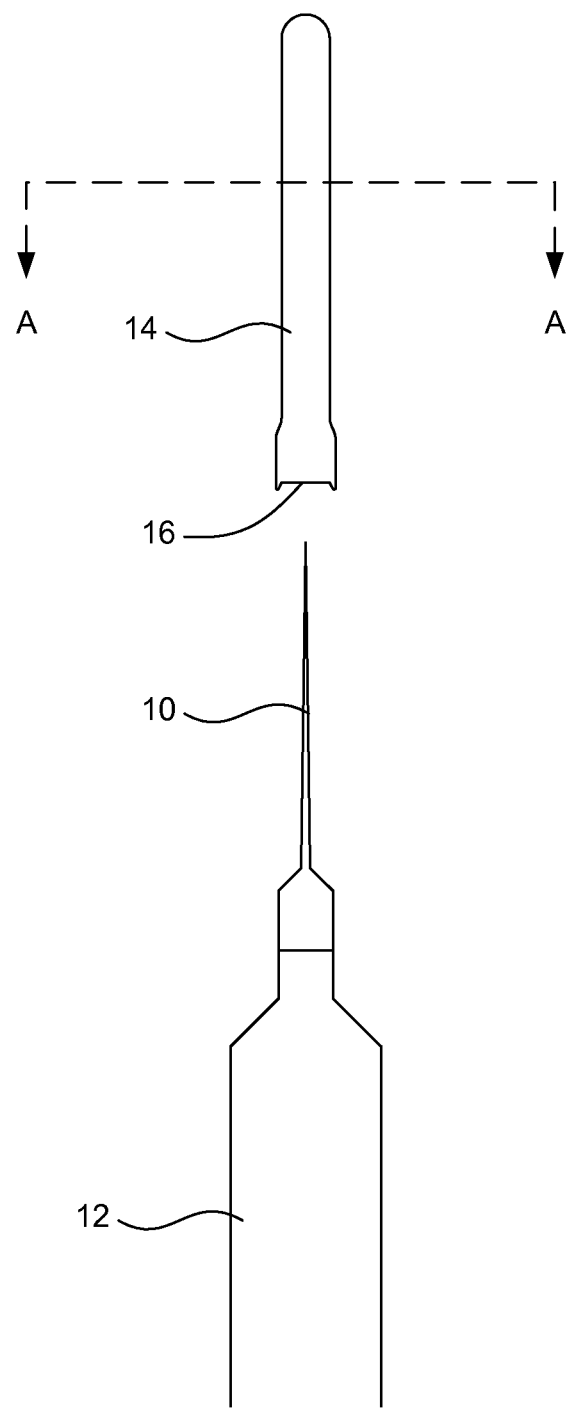
FIG. 1 shows a plan view of a representative hypodermic needle and cap.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide a containment system for encapsulating a sharp medical instrument. The containment system includes a container formed of a durable and flexible material having a rim defining an open end configured to receive a sharp portion of the medical instrument and an interior surface, wherein at least a portion of the interior surface is covered with a strong adhesive such that opposing sides of the container can be deformed under external pressure to cause the opposing sides to come together surrounding the sharp portion such that the sharp portion is substantially permanently retained inside the container by the adhesive.

The sharp medical instrument may be a hypodermic needle, and the container a cap of the needle. The adhesive may be protected by a removable covering. The removable covering may be attached to a pull tab that extends through an opening in an end of the container distal the open end defined by the rim.

The container may have a cross-section having a major axis and a minor axis, and wherein the container is deformable in the direction of the minor axis to permit opposite sides of the container to compress along the minor axis until they contact one another. The container may have a generally-oval cross section.

The adhesive may be an adhesive tape disposed on the interior surface. The adhesive tape may be protected by a removable covering attached to a pull tab that extends through an opening in an end of the container distal the open end defined by the rim.

Further embodiments of the invention provide a method for safely and permanently encapsulating a sharp medical instrument. The method includes inserting the sharp medical instrument into a container having a rim defining an open end configured to receive a sharp portion of the medical instrument and an interior surface, wherein at least a portion of the interior surface is covered with a strong adhesive. The method also includes causing opposing sides of the container to be deformed under external pressure and to be brought together surrounding the sharp portion such that the sharp portion is substantially permanently retained inside the container by the adhesive.

The sharp medical instrument may be a hypodermic needle, and the container a cap for the needle.

The method may also include removing a removable covering protecting the adhesive before deforming the opposing sides of the container. Removing the removable covering may include pulling a pull tab that extends through an opening in an end of the container distal the open end defined by the rim.

The container may have a cross-section having a major axis and a minor axis, and wherein the container is deformable in the direction of the minor axis to permit opposite sides of the container to compress along the minor axis until they contact one another.

Embodiments of the invention provide a containment system for encapsulating a hypodermic needle. The system includes a cap formed of a durable and flexible material having a rim defining an open end configured to receive the needle and an interior surface, wherein at least a portion of the interior surface is covered with a strong adhesive such that opposing sides of the cap can be deformed under external pressure to cause the opposing sides to come together surrounding the needle such that the needle is substantially permanently retained inside the cap by the adhesive.

The adhesive may be protected by a removable covering. The removable covering may be attached to a pull tab that extends through an opening in an end of the cap distal the open end defined by the rim.

The cap may have a cross-section having a major axis and a minor axis, wherein the cap is deformable in the direction of the minor axis to permit opposite sides of the cap to compress along the minor axis until they contact one another. The cap may have a generally-oval cross section.

The adhesive may be an adhesive tape disposed on the interior surface. The adhesive tape may be protected by a removable covering attached to a pull tab that extends through an opening in an end of the cap distal the open end defined by the rim.

FIG. 1 illustrates one system for encapsulating a sharp portion of a sharp medical instrument, namely a hypodermic needle 10 affixed to a syringe 12. The needle 10 and syringe 12 are in all respects essentially identical to known syringes and needles, and permit delivery of liquids from the syringe 12 through a hollow channel of the needle 10 into a target tissue, vessel, etc. As with any needle, it is desirable to prevent accidental needle sticks of the needle 10 before and after the needle 10 is to be used, and it is also desirable to prevent re-use of the needle 10 after its initial intended use to prevent the spread of blood-borne pathogens and the like. It is also desirable to prevent re-use of the needle 10, as re-use is commonly associated with illicit drug use, and is therefore even more likely to be associated with pathogen transmission.

Therefore, associated with the needle 10 and the syringe 12 is a cap 14, which is one example of a container for receiving a sharp portion of a sharp medical instrument. As with standard syringe caps, the cap 14 is sized and formed so as to be removably affixable to the syringe 12 covering the needle 10. The cap 14 may be affixable to the syringe 12 using any known system or method, including a snap fit, a frictional engagement, or a threaded engagement between the cap 14 and the syringe 12.

The cap 14 may be constructed in many ways similarly to known caps, covers, and containers for syringes, and may be made, for example, of a durable but deformable plastic material. The cap 14 may typically be provided covering the needle 10, either with the syringe 12 or as a needle system to be affixed to the syringe 12, as is typically done with existing needle and cap or needle, syringe and cap systems. Thus, embodiments of the invention may be advantageously used in conjunction with existing needles and syringes in all respects without modification to the existing needles and syringes, and without requiring the use of multiple caps for each needle and syringe.

Figure 2:
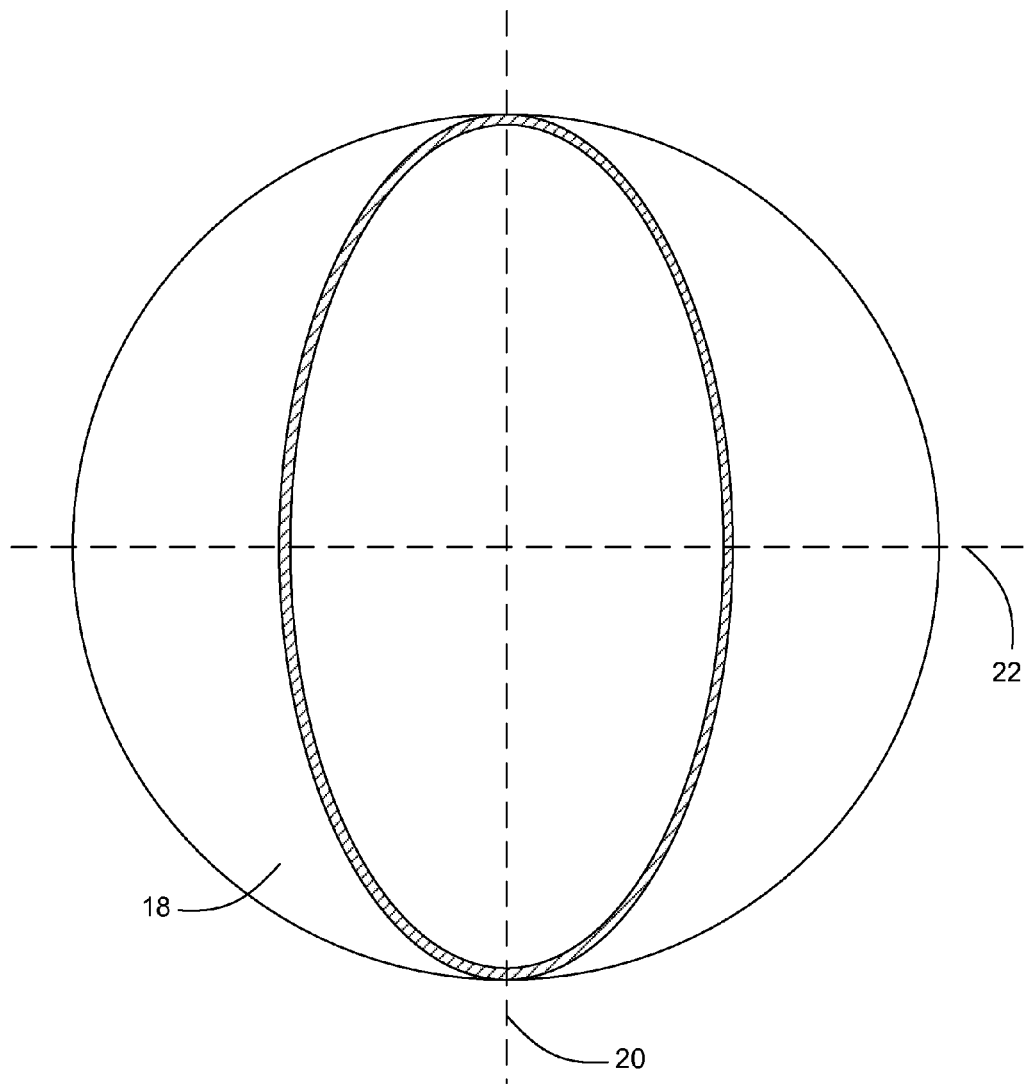
FIG. 2 shows a cross-sectional view of a representative cap.

The cap 14 includes a rim 16 defining an open end of the cap 14, the open end being configured to receive the needle 10 into the cap 14. FIG. 2 shows a cross-sectional view of one embodiment of the cap 14, taken along the line A-A shown in FIG. 1. As may be seen in FIG. 2, the cap 14 has a round base 18 for engaging a round portion of the syringe 12; however, at the location of the cross section, the cap 14 may have a generally-oval cross section, with a major axis 20 and a minor axis 22. Because the cap 14 is made of a deformable material, the cap 14 is deformable in the direction of the minor axis 22 such that opposing walls or sides of the cap 14 may be deformed under pressure and brought to contact each other. When a strong adhesive is disposed on at least one of the sides of the interior surface of the cap 14, the adhesive may substantially permanently join the two sides of the cap 14 together, thereby trapping and containing the needle 10 therein. This containment prevents needle sticks and re-use of the needle 10.

The adhesive may take any of a variety of forms, and any adhesive known in the art to provide sufficient adhesive qualities to perform the functions described herein may be used. In some embodiments, the adhesive is an adhesive tape disposed on the interior surface of the cap 14. In some embodiments, the adhesive tape is protected by a removable covering 24, as is illustrated in various embodiments in FIG. 3. The removable covering 24 is then removed at the time of use to expose the adhesive.

Figure 3:
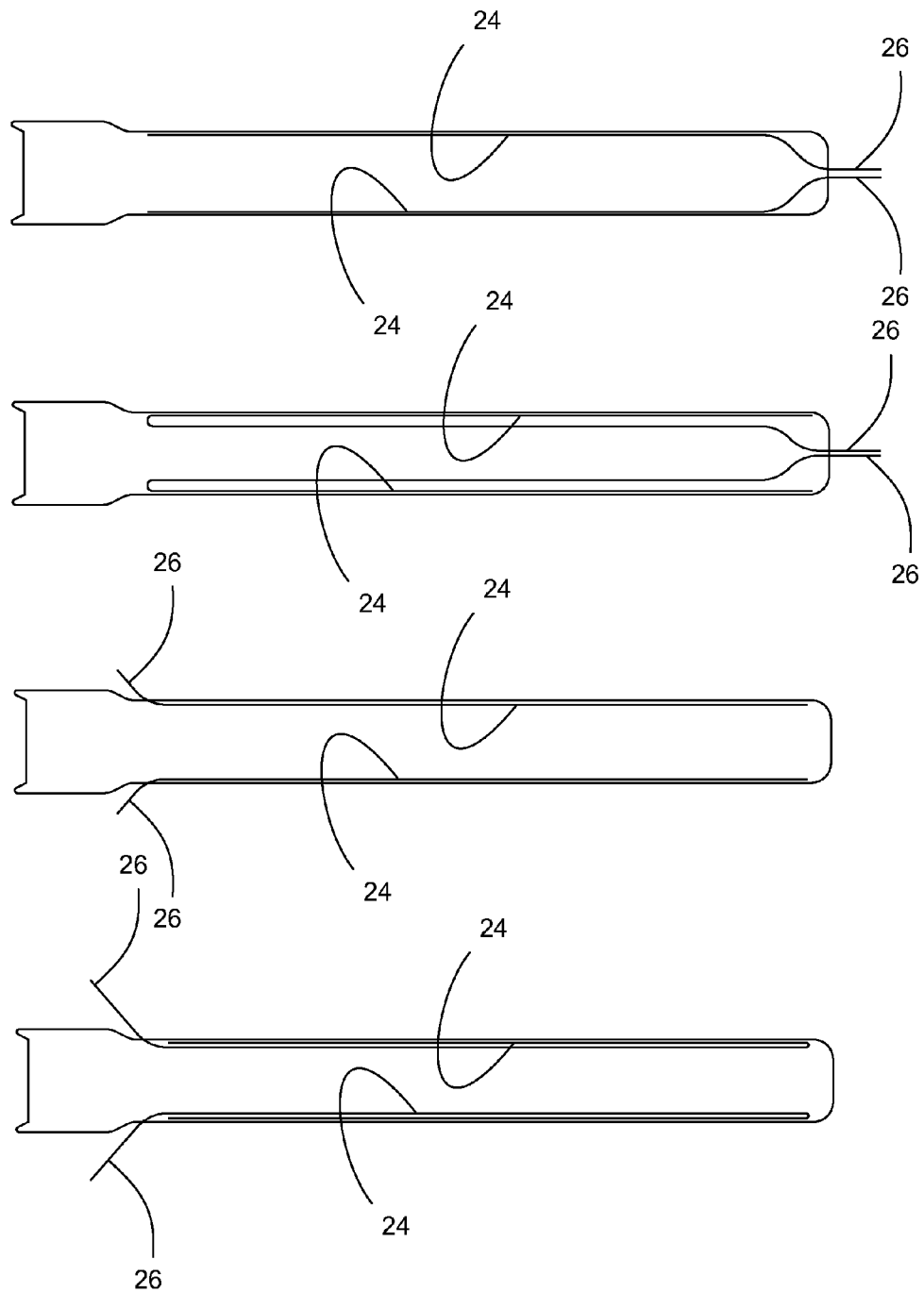
FIG. 3 shows a plan view of four representative caps with adhesive coverings therein.

For example, the removable covering 24 may include a pull tab 26 that extends externally of the cap 14 through a hole in the cap 14, such that the pull tab 26 may be grasped and pulled at the time of use to expose the adhesive. There are many potential ways in which the covering 24 may be disposed and the pull tab 26 provided, and FIG. 3 illustrates four representative manners in which the covering 24 and pull tab 26 may be provided. It should be understood that the proportions shown in FIG. 3 are provided for ease of illustration only.

When the needle 10 is to be used, the cap 14 is removed and the needle 10 is used as normal. Then, the cap 14 is replaced, the adhesive is exposed if necessary (such as by pulling on pull tab 26 to remove the covering 24), and the cap 14 is pressed together or crushed along its minor axis 22, thereby permanently encapsulating the needle to prevent needle sticks and reuse of the needle 10.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A containment system for encapsulating a sharp medical instrument comprising:
   a container formed of a durable and flexible material comprising:
      a rim defining an open end configured to receive a sharp portion of the medical instrument; and
      an interior surface, wherein at least a portion of the interior surface is covered with a strong adhesive such that opposing sides of the container can be deformed under external pressure to cause the opposing sides to come together surrounding the sharp portion such that the sharp portion is substantially permanently retained inside the container by the adhesive;
      wherein the adhesive is protected by a removable covering attached to a pull tab that extends through an opening in an end of the container distal the open end defined by the rim.

2. A containment system as recited in claim 1, wherein the sharp medical instrument comprises a hypodermic needle.

3. A containment system as recited in claim 1, wherein the container comprises a cross-section having a major axis and a minor axis, and wherein the container is deformable in the direction of the minor axis to permit opposite sides of the container to compress along the minor axis until they contact one another.

4. A containment system as recited in claim 3, wherein the container comprises a generally-oval cross section.

5. A containment system as recited in claim 1, wherein the adhesive comprises an adhesive tape disposed on the interior surface.

6. A containment system as recited in claim 5, wherein the adhesive tape is protected by a removable covering attached to a pull tab that extends through an opening in an end of the container distal the open end defined by the rim.

7. A method for safely and permanently encapsulating a sharp medical instrument, the method comprising:
   inserting the sharp metal instrument into a container, the container comprising:
      a rim defining an open end configured to receive a sharp portion of the medical instrument; and
      an interior surface, wherein at least a portion of the interior surface is covered with a strong adhesive;
   removing a removable covering protecting the adhesive, comprising pulling a pull tab that extends through an opening in an end of the container distal the open end defined by the rim; and
   causing opposing sides of the container to be deformed under external pressure and to be brought together surrounding the sharp portion such that the sharp portion is substantially permanently retained inside the container by the adhesive.

8. A method as recited in claim 7, wherein the sharp medical instrument comprises a hypodermic needle.

9. A method as recited in claim 7, wherein the container comprises a cross-section having a major axis and a minor axis, and wherein the container is deformable in the direction of the minor axis to permit opposite sides of the container to compress along the minor axis until they contact one another.

10. A containment system for encapsulating a hypodermic needle comprising:
   a cap formed of a durable and flexible material comprising:
      a rim defining an open end configured to receive the needle; and
      an interior surface, wherein at least a portion of the interior surface is covered with a strong adhesive such that opposing sides of the cap can be deformed under external pressure to cause the opposing sides to come together surrounding the needle such that the needle is substantially permanently retained inside the cap by the adhesive;
   wherein the cap comprises a generally-oval cross-section having a major axis and a minor axis, and wherein the cap is deformable in the direction of the minor axis to permit opposite sides of the cap to compress along the minor axis until they contact one another.

11. A containment system as recited in claim 10, wherein the adhesive is protected by a removable covering.

12. A containment system as recited in claim 10, wherein the removable covering is attached to a pull tab that extends through an opening in an end of the cap distal the open end defined by the rim.

13. A containment system as recited in claim 10, wherein the adhesive comprises an adhesive tape disposed on the interior surface.

14. A containment system as recited in claim 13, wherein the adhesive tape is protected by a removable covering attached to a pull tab that extends through an opening in an end of the cap distal the open end defined by the rim.

* * * * *